(12) United States Patent
Stormbom et al.

(10) Patent No.: US 6,809,528 B1
(45) Date of Patent: Oct. 26, 2004

(54) METHOD AND APPARATUS FOR MEASURING WATER CONTENT

(75) Inventors: Lars Stormbom, Vantaa (FI); Matti Lyyra, Vantaa (FI); Jukka Leppänen, Klaukkala (FI)

(73) Assignee: Vaisala Oyj, Helsinki (FI)

( * ) Notice: Subject to any disclaimer, the term of this patent is extended or adjusted under 35 U.S.C. 154(b) by 0 days.

(21) Appl. No.: 10/009,730

(22) PCT Filed: Jun. 15, 2000

(86) PCT No.: PCT/FI00/00542

§ 371 (c)(1),
(2), (4) Date: Mar. 12, 2002

(87) PCT Pub. No.: WO00/79256

PCT Pub. Date: Dec. 28, 2000

(30) Foreign Application Priority Data

Jun. 17, 1999 (FI) .................................................. 991391

(51) Int. Cl.[7] .............................................. G01R 27/26
(52) U.S. Cl. ........................ 324/664; 324/670; 324/698
(58) Field of Search .................................. 324/664, 694, 324/698, 699, 670, 684, 685, 663, 690

(56) References Cited

U.S. PATENT DOCUMENTS

| 4,129,501 A | 12/1978 | Haynes ........................ 210/689 |
| 5,331,287 A | 7/1994 | Yamagishi et al. ......... 324/724 |
| 5,642,098 A | 6/1997 | Santa Maria et al. ....... 340/618 |
| 5,644,239 A | 7/1997 | Huang et al. ............... 324/439 |
| 5,656,767 A | 8/1997 | Garvey, III et al. ....... 73/61.44 |

FOREIGN PATENT DOCUMENTS

| DE | 196 47 201 C1 | 2/1998 |
| EP | 0 141 636 A1 | 5/1985 |
| WO | 98/46984 A2 | 10/1998 |
| WO | 99/23469 A1 | 5/1999 |

Primary Examiner—Guy J. Lamarre
Assistant Examiner—James C. Kerveros
(74) Attorney, Agent, or Firm—Birch, Stewart, Kolasch & Birch, LLP

(57) ABSTRACT

A method and apparatus for measuring the water content of a liquid, including a method step for electrically measuring the property of the liquid for one parameter. The properties of the liquid are measured at least substantially simultaneously by another electrical method, where the properties of the liquid are measured using both a relative-value and an absolute-value measurement method.

16 Claims, 1 Drawing Sheet

# US 6,809,528 B1

METHOD AND APPARATUS FOR MEASURING WATER CONTENT

CROSS-REFERENCE TO RELATED APPLICATION

This application is the national phase under 35 U.S.C. § 371 of PCT International Application No. PCT/FI00/00542 which has an International filing date of Jun. 15, 2000, which designated the United States of America and was published in English.

BACKGROUND OF THE INVENTION

1. Field of the Invention

The invention relates to a method according to the preamble of claim 1 for measuring the water content of a liquid.

2. Description of Background Art

The invention also relates to an apparatus for measuring the water content of a liquid.

U.S. Pat. No. 5,331,287 describes a sensor, wherein interdigitated electrodes (finger electrodes are coated with a conducting polymer. Water contained in the oil hydrates the polymer and thus modifies its conductivity. Also detects possible acids by way of protonation.

U.S. Pat. No. 5,642,098 discloses a ring oscillator circuit, wherein electrical properties of the oil are measured with a number of measurement heads which measure the same parameter.

U.S. Pat. No. 5,644,239 measures the electrical conductivity of a liquid (oil) at two elevated temperatures. The technique may be complemented with a possible optical measurement of oil opacity. A "figure of quality" may then be computed for the oil from these parameters.

U.S. Pat. No. 5,656,767 describes a sensor system for measuring the change of an electrical parameter value (e.g., capacitance) in oil as a function of time. The same oil at a clean (dry) state may be used as a reference value. The same technique may be varied in multiple ways, e.g., by heating the oil sample.

Conventional techniques are handicapped in many aspects. Common methods for sensing absolute water volume content over the entire range of 0–100% are the measurement of the dielectric coefficient and measurement of IR absorption. Both of these methods have in common that they require a zeroing step of the measurement system, whereby the reading must be reset to zero water content when the sensor is brought to measure an entirely dry (water-free) liquid. This step can be accomplished as a discrete zeroing operation or by using a sample of entirely dry oil in the sensor as a reference.

An additional complication arises therefrom that such a zero setting is typically dependent on the temperature.

Also other factors besides the water content may affect the zero-value with the aging of the liquid.

Methods measuring the absolute water content are favored at high water contents (in the order of several per cent).

At lower water contents, problems generally arise from the marginal detection threshold and offset uncertainty (error of zero setting).

A relative value (aw) measurement method gives information on the water content value in relation to that of a fully saturated situation. However, a conversion to the volume percentage value of absolute water content remains undefined unless a conversion factor for the liquid being measured is known. The aw measurement method is suitable for use at low water content levels (nonsaturated and not emulsified), whereby the measurement has a sufficiently high sensitivity. Moreover, the method is free from zeroing problems.

BRIEF SUMMARY OF THE INVENTION

It is an object of the present invention to overcome the drawbacks of the above described techniques and to provide an entirely novel type of method and apparatus for measuring the water content of a liquid.

The goal of the invention is achieved by way of measuring the water content of the oil/liquid using two different methods simultaneously, whereby the measurement technique is based on an absolute value measurement method complemented with a relative value measurement method.

The method and apparatus of the present invention offer significant benefits.

The combination of an absolute value measurement method with a relative value measurement method (aw-type of measurement) makes it possible to eliminate the need for a zeroing step in the absolute value measurement.

By way of performing a sequence of rapidly repeated measurements at different temperatures, it is also possible to eliminate errors caused by temperature variations.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE PREFERRED EMBODIMENTS

Figure 1:
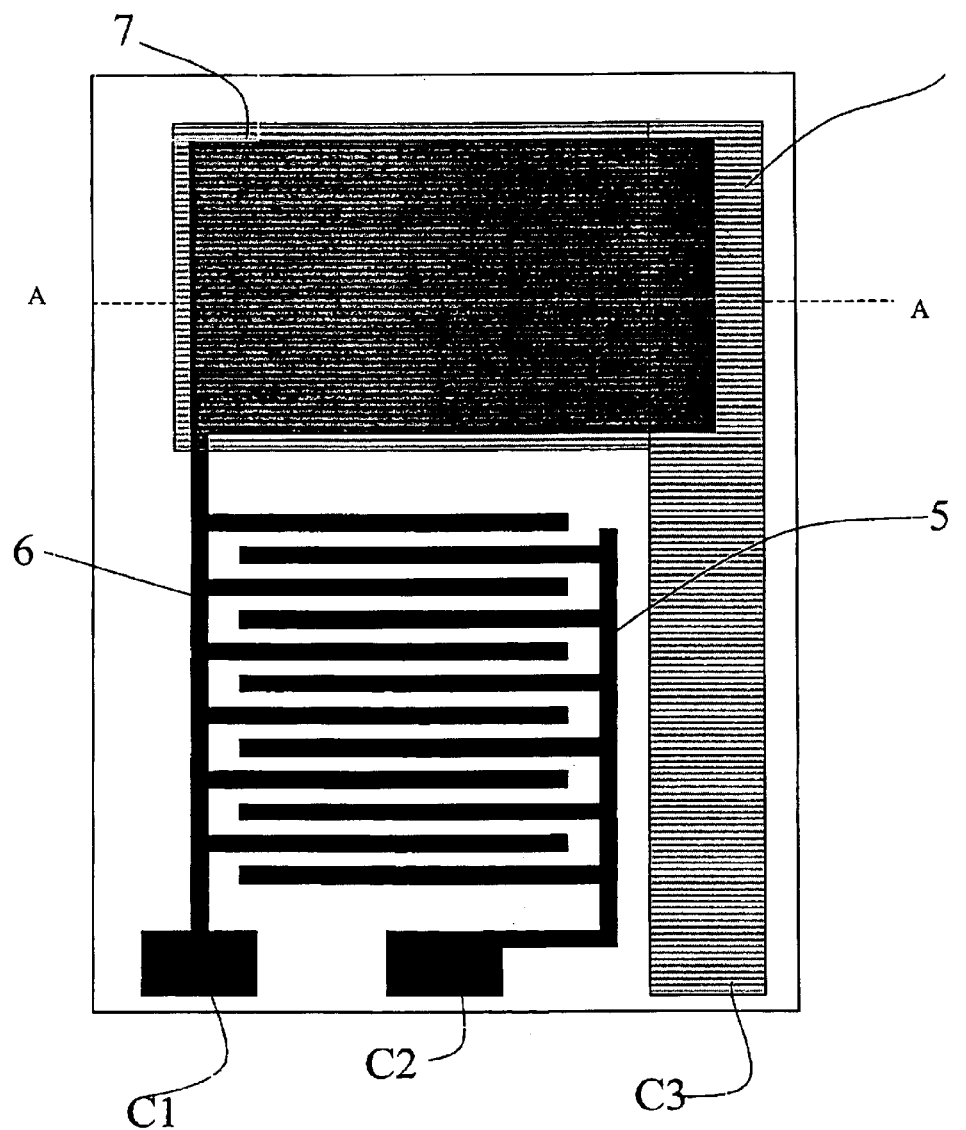
FIG. 1 shows a top view of an embodiment of an electrode structure according to the invention.
Figure 2:
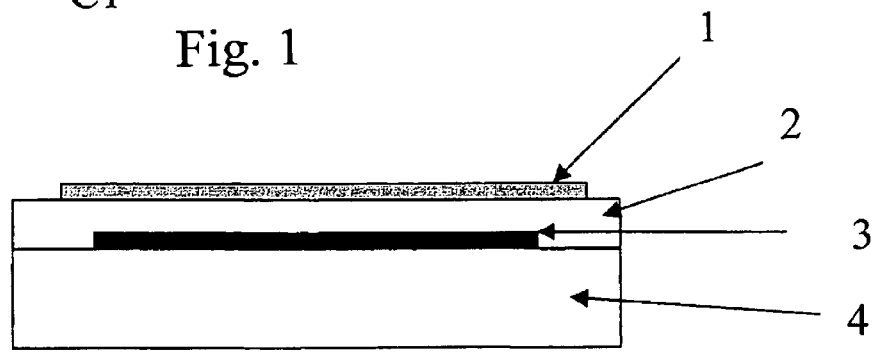
FIG. 2 shows a sectional view of the sensor structure of FIG. 1 along line A—A.

As shown in FIGS. 1 and 2, the embodiment according to the invention can be implemented using a structure, wherein onto the surface of a substrate 4 is formed a combination of three electrodes. The surface of the substrate 4 has directly deposited thereon a pair 3 of bottom electrodes formed by electrodes 5 and 6. In the illustrated case, the electrodes are shaped into finger electrodes, more specifically disposed as so interdigitated electrodes, whereby the interelectrode surface is maximized by using an electrode structure having the finger electrodes displaced between each other. The length of the adjacent edges of the interdigitated electrodes 5 and 6 is equivalent to the area of superimposed electrodes in a planar capacitor. The width and interelectrode gap of the electrodes 5 and 6 typically are in the range of 5 to 500 micrometers. In addition to its interdigitated finger electrode portion, the electrode 6 has a planar area 7. Furthermore, the electrodes 5 and 6 include contact pad areas C1 and C2 for connection of the electrodes to measurement means. Onto the bottom electrode pair 3 is deposited a polymer layer 2 having a thickness of 0.5–5 micrometer typical. The area of the polymer layer 2 may also be extended over the inter-digitated finger electrode structure 5 and 6, whereby it also functions as a passivation layer and reduces the effect of conducting particles contained in the liquid sample on the measurement result. Onto the polymer layer 2 is deposited a water-permeable top electrode 1 with a contact pad area C3 for external connections. The top electrode 1 is aligned above the rectangular solid area 7 of the electrode 6 in order to form a planar capacitor structure.

The structure illustrated in FIGS. 1 and 2 is utilized as follows. The dielectric coefficient of the liquid under measurement is measured over the contacts C1 and C2 of the electrodes 5 and 6. Respectively, the relative value measurement is performed over the electrodes 6 and 1, that is from the contacts C1 and C3.

Advantageously, the liquid whose water content is measured is oil, but the water content measurement according to the invention may also be performed on other liquids such as a hydraulic fluid, gasoline or a coolant as well.

According to the invention, the measurement of the activity of water can be carried out as follows.

Firstly, it must be noted that the water activity measurement is only an exemplifying embodiment of the relative value measurement technique according to the invention.

As shown in FIGS. 1 and 2, the sensor may comprise a polymer layer 2 deposited between two electrodes as an element, whose absorbency of water is a function of the activity of water in its immediate environment. Typically, such sensors are used as relative humidity transducers, for example. This type of measurement method is characterized in that the measurement result indicates the degree of water activity, that is:

$$aw = F(ppm/ppm_s(T)), \quad (1)$$

where ppm=volumetric proportion of water in solution×$10^6$ $ppm_s$=volumetric proportion of water in saturated solution×$10^6$ The function F may for example be assumed to have a linear nature, whereby:

$$aw = ppm/ppm_s(T) \quad (2)$$

The value of aw varies from 0 (entirely dry liquid) to 1 (entirely saturated water solution).

Hence, a mere water activity measurement gives information on how close the situation is either to an emulsified state or a water-separation state. However, when the state of emulsification or water separation is reached, the value of water activity becomes very close to 1, whereby no information on the state of the liquid can be obtained. Nevertheless, the method can render at values of aw<0.9 in a very sensitive manner such oil/liquid-independent information that, for example, is related to the lubrication properties of the measured sample.

At room temperature, the value of $ppm_s$ may vary from 20 ppm for a basic oil having no additives to values above 10,000 ppm for lubrication oils rich with additives.

Next, the measurement technique of the dielectric coefficient is elucidated in more detail. The measurement of the dielectric coefficient is only one exemplifying embodiment of the absolute-value concentration measurements possible within the scope of the invention.

In the measurement of the dielectric coefficient of a liquid, the sensor may be implemented either using the interdigitated electrode (finger-electrode) structure according to FIGS. 1 and 2 or, alternatively, formed into a coaxial pair of electrodes brought into contact with the liquid to be measured. The output signal of the sensor is dependent on both the dielectric coefficient and water content of the liquid under measurement:

$$\epsilon_r = \epsilon_0 + F(ppm) \quad (3)$$

where $\epsilon_0$=dielectric coefficient of entirely dry liquid,

F(ppm)=a function dependent on the water content. Over a limited range of water content, the function may be assumed to be linear, that is:

$$\epsilon_r = \epsilon_0 + a \times ppm \quad (4)$$

where a=constant independent of the liquid type.

An advantage of the dielectric coefficient measurement technique is that it covers the entire possible measurement range from 0 to 100 vol-% water. A disadvantage of the method is that its sensitivity at the low end of water content (where the greatest interest usually lies) is low and that the value of $\epsilon_0$ must be known. Typically, the measurement system is calibrated using dehydrated oil as a standard.

If both of the above-described measurement techniques are employed simultaneously, a number of different calibration techniques can be used for a given liquid.

If the liquid is known by the value of its $ppm_s(T)$, the following approach is possible:

First, the values of aw and $\epsilon_r$, are measured simultaneously. If aw is less than 1, formulas 2 and 4 may be assumed to be valid.

Then, the combination of formulas 2 and 4 can be solved for $\epsilon_0$ and ppm. It is also possible to estimate the value of $ppm_s(T)$ if the type of the liquid is known, whereby the result thus obtained, however, remains slightly more inaccurate.

If the value of $ppm_s(T)$ of the liquid is unknown, the following procedure can be carried out:

The sensor output is measured at two (unknown) water content values. If the value of aw is smaller than 1 in both cases, an equation group of four equations and four unknown variables is obtained, which means the equations can be solved in unique manner. Assigning subindices 1 and 2 for the measurement results of the two sessions, respectively, the following formula can be written:

$$\epsilon_0 = (aw_2 \times \epsilon_{r1} - aw_1 \times \epsilon_{r2})/(aw_2 - aw_1) \quad (5)$$

This procedure may also be arranged to take place automatically during the continuous function of the measurement apparatus if the water content of the liquid under measurement varies.

If the measurement data is collected by more than two pairs of values, the unknown terms can be fitted to the data using, e.g., the least squares method.

The benefit of the latter technique is that possible changes in the values of $\epsilon_0$ or $ppm_s(T)$ due to temperature variations or aging/soiling of the liquid can be compensated for. In fact, the changes detected in so serve as an indicator of aging in oil.

If the temperature of an oil sample or, respectively, of a sample flow, is changed so rapidly that the water content of the sample can be assumed to stay substantially unchanged, it is possible to determine the temperature dependence of the dielectric coefficient of an entirely dry liquid by way of measuring essentially simultaneously the E, and temperature of the liquid at least two temperatures.

For example it can be assumed assuming that so is a linear function with temperature:

$$\epsilon_r = b0 + b1 \times T + a \times ppm \quad (6)$$

whereby the following formula can be formed $$\epsilon_r(T2) - \epsilon_r(T2) = b1 \times (T2-T1) \quad (7)$$

wherefrom the coefficient b1 can be solved. Also in this case, it is possible to collect values at a greater number of temperatures and then fit the measurement results with a the help of the least squares method. This technique gives a continuously reliable parameter estimate value for so as the temperature varies.

Also the temperature dependence of $ppm_s(T)$ can be determined simultaneously. Over a limited temperature range, a general assumption may be made as:

$$ppm_s(T) = c0 \times e^{(c1 \times T)} \quad (8)$$

where $c0$ = value of $ppm_s$ at T=0° C.

$c1$ = coefficient of temperature dependence.

Then, the value of c1 can be solved by way of measuring aw at at least two temperatures with the assumption that the water content of the liquid remains unchanged during the measurements:

$$c1 = LN(aw1/aw2)/(T2-T1) \quad (9)$$

Advantageously, these two determinations may be carried out simultaneously.

According to a preferred embodiment of the invention, the zeroing operation is performed automatically each time the measurement of aw gives a sufficiently low value. The lower the value of aw the more accurate the zeroing operation. The uncertainty of the method is associated with the value of $ppm_s(T)$ that is dependent on the type of liquid under measurement and thus can be obtained by an "intelligent guess".

According to another preferred embodiment of the invention, two samples of the liquid/oil having different water contents are taken. Then, the measurement system may intentionally be set to measure two samples of different water contents or, alternatively, gradual accumulation of data from the measured process is utilized, whereby the natural variation of water content in the monitored process is availed of. This approach also gives a value for $ppm_s(T)$ on the basis of which it is possible according to the invention to compute from the measured value of aw the correct value of ppm without resorting to an "intelligent guess".

If a continuous data collection from the monitored process is performed using simultaneously a sliding-window technique for "dumping" obsolete data, it is also possible to compensate for changes in both the value of $ppm_s$ and $\epsilon_0$ due to aging of the liquid/oil.

In the case that the process also is subjected to temperature changes, the temperature dependencies of $ppm_s$ and $\epsilon_0$ can also be resolved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring water content of a liquid, comprising the steps of:

electrically measuring properties of the liquid at least substantially simultaneously and repeatedly by an absolute-value measurement method in order to determine a dielectric coefficient of the liquid, and by a direct relative-value measurement method in order to determine a relative water content of the liquid.

2. The method according to claim 1, wherein a temperature dependence of the dielectric coefficient of an entirely dry liquid is determined by measuring essentially simultaneously the $(\epsilon_r)$ aw and the temperature of the liquid at at least two temperatures, wherein $(\epsilon_r) = (\epsilon_0) + F(ppm)$, $(\epsilon_0)$ = dielectric coefficient of entirely dry liquid, F(ppm) = a function dependent on the water contents, aw = Fppm/$ppm_s(T)$, ppm = volumetric proportion of water in solution×$10^6$, and $ppm_s$ = volumetric proportion of water in saturated solution×$10^6$.

3. The method according to claim 1, wherein the measuring steps are repeated at two different temperatures in rapid succession so that the water content of the liquid stays at least substantially constant.

4. The method according to claim 1, wherein changes in results of water content measurements due to aging of the liquid are compensated for by virtue of using only most recent data of a measurement history for compensation for changes in a response of the measurement system.

5. The method according to claim 1, wherein aging of said liquid, advantageously oil, is indicated on a basis of changes in the value of the dielectric coefficient of entirely dry liquid ($\epsilon_0$).

6. The method according to claim 1, wherein, in the step of measuring the relative water content, an auxiliary medium is used for absorbing the water contained in the liquid being measured.

7. The method according to claim 6, wherein said auxiliary medium is a thin-film polymer layer.

8. The method according to claim 6, wherein the water content of said auxiliary medium is determined by measuring its dielectric coefficient.

9. An apparatus for measuring water content of a liquid, said apparatus comprising:

first electrical sensor means for measuring an absolute water content of the liquid being sensitive to changes in a dielectric coefficient;

second electrical sensor means for directly measuring a relative water content of the liquid; and means for controlling the first and the second electrical sensor means such that the properties of the liquid are electrically measured at least substantially simultaneously and repeatedly.

10. The apparatus according to claim 9, wherein the first and the second sensor means sensitive to changes in the dielectric coefficient are formed by two interdigitated finger electrodes.

11. The apparatus according to claim 9, wherein the sensor means is adapted for measuring the relative water content contains an auxiliary medium capable of absorbing water contained in the liquid being measured.

12. The apparatus according to claim 11, wherein said auxiliary medium is a thin-film polymer layer.

13. The apparatus according to claim 9, the first electrical sensor means and the second electrical sensor means forming a first sensor pair adapted to measure of the dielectric coefficient, and one electrode of said first sensor pair also forming a part of a second sensor pair adapted to measure the relative water content.

14. The apparatus according to claim 13, wherein the one electrode is formed by a center pin and a jacket having a net structure that is permeable to water.

15. The apparatus according to claim 13, wherein the apparatus contains means adapted to measure the dielectric coefficient of said auxiliary medium, whereupon the relative water content of said auxiliary medium can be determined.

16. The apparatus according to claim 9, wherein the first electrical sensor means sensitive to the dielectric coefficient is formed by a coaxial structure.

\* \* \* \* \*